(12) United States Patent
Fetzer et al.

(10) Patent No.: US 7,975,549 B2
(45) Date of Patent: Jul. 12, 2011

(54) METHOD, APPARATUS AND SYSTEM FOR INSPECTING A WORKPIECE HAVING A CURVED SURFACE

(75) Inventors: Barry A. Fetzer, Renton, WA (US); Hien T. Bui, Kent, WA (US)

(73) Assignee: The Boeing Company, Chicago, IL (US)

( * ) Notice: Subject to any disclaimer, the term of this patent is extended or adjusted under 35 U.S.C. 154(b) by 450 days.

(21) Appl. No.: 11/765,131

(22) Filed: Jun. 19, 2007

(65) Prior Publication Data

US 2008/0314154 A1    Dec. 25, 2008

(51) Int. Cl.
G01N 29/04    (2006.01)
(52) U.S. Cl. ............... 73/626; 73/628; 73/644
(58) Field of Classification Search .......... 73/628, 73/637, 638, 640, 644, 626
See application file for complete search history.

(56) References Cited

U.S. PATENT DOCUMENTS

| | | | | |
|---|---|---|---|---|
| 3,663,842 | A | * | 5/1972 | Miller ............ 310/338 |
| 4,183,249 | A | * | 1/1980 | Anderson ........... 73/626 |
| 4,195,530 | A | * | 4/1980 | Ross et al. ........ 73/638 |
| 4,472,973 | A | * | 9/1984 | Sugai et al. ....... 73/626 |
| 4,807,476 | A | | 2/1989 | Cook et al. |
| 5,001,674 | A | * | 3/1991 | Kawasaki .......... 367/13 |
| 5,392,652 | A | | 2/1995 | Levesque et al. |
| 5,913,243 | A | | 6/1999 | Hopeck et al. |
| 6,658,939 | B2 | | 12/2003 | Georgeson et al. |
| 6,993,971 | B2 | | 2/2006 | Bossi et al. |
| 7,516,664 | B2 | * | 4/2009 | Meier et al. .......... 73/644 |
| 2007/0239018 | A1 | | 10/2007 | Fetzer |

FOREIGN PATENT DOCUMENTS

JP    62030951 A    2/1987

OTHER PUBLICATIONS

J. Krautkramer et al., Ultrasonic Testing of Materials, 3rd Edition, Springer Verlag, New York, 1983, pp. 290-293.*
International Search Report for PCT/US2008/067442, dated Oct. 6, 2008.

* cited by examiner

*Primary Examiner* — John E Chapman
(74) *Attorney, Agent, or Firm* — Alston & Bird LLP

(57) ABSTRACT

A non-destructive inspection method, apparatus and system are provided for inspecting a workpiece having a curved surface with at least one predefined radius of curvature. The apparatus, such as an inspection probe, includes a plurality of transducer elements positioned in an arcuate configuration having a predefined radius of curvature and a curved delay line. The curved delay line has an outer arcuate surface having a predefined radius of curvature that matches the predefined radius of curvature of the transducer elements. The curved delay line also has an inner arcuate surface that has at least one predefined radius of curvature that matches the at least one predefined radius of curvature of the curved surface of the workpiece. In addition to the inspection probe, the system includes an excitative source for triggering the transducer elements to emit signals into the workpiece and a computing device to receive the return signals.

29 Claims, 4 Drawing Sheets

METHOD, APPARATUS AND SYSTEM FOR INSPECTING A WORKPIECE HAVING A CURVED SURFACE

FIELD OF THE INVENTION

Embodiments of the present invention relate generally to non-destructive inspection devices and methods and, more particularly, to non-destructive inspection devices and methods for inspecting workpieces having curved surfaces.

BACKGROUND OF THE INVENTION

Non-destructive inspection (NDI) of structures involves thoroughly examining a structure without harming the structure or requiring its significant disassembly. Non-destructive inspection is typically preferred to avoid the schedule, labor and costs associated with the removal of a part for inspection, as well as avoidance of the potential for damage to the structure during such disassembly and subsequent reassembly. Non-destructive inspection is advantageous for many applications in which a thorough inspection of the exterior and/or interior of a structure is required. For example, non-destructive inspection is commonly used in the aircraft industry to inspect aircraft structures for any type of internal or external structural inconsistencies in the structure. Inspection may be performed during manufacturing or after the completed structure has been put into service, including field testing, to validate the integrity and fitness of the structure.

Various types of sensors may be utilized to perform non-destructive inspection. One or more sensors may move over the structure to be examined and receive data regarding the structure from which internal structural inconsistencies can be identified. For example, a pulse-echo, through-transmission or shear wave sensor may be utilized to obtain ultrasound data that may be utilized for thickness gauging, detection of laminar defects and porosity and/or crack detection in the structure. Resonance, pulse echo or mechanical impedance sensors may also be utilized to provide indications of voids or porosity, such as in adhesive bond lines of the structure. The data acquired by the sensors is typically processed by a computing device, and the processed data may be stored and/or presented to a user via a display.

Certain types and configurations of structures provide particular challenges during efforts to non-destructively inspect the structure. For example, some structures include a curved surface which may render efforts to non-destructively inspect the curved portion of the workpiece more difficult or at least render the results less detailed than desired. The difficulties presented by non-destructive inspection of structures having curved surfaces is particularly apparent in instances in which the curved surface is a compound curve having different portions with different respective radii of curvature. While a variety of structures having curved surfaces may present challenges for non-destructive inspection, one particular example is a composite structure that defines a shear tie, such as utilized during the manufacture of aircraft. In this regard, a shear tie defines an arc spanning about 90° and includes two or more portions that each have a different respective radius of curvature.

In order to inspect a workpiece having a curved surface, such as a shear tie, inspection probes are utilized that include a plurality of transducers positioned in an arcuate fashion in order to introduce ultrasonic signals into the structure and to receive ultrasonic signals returning from the workpiece. As a result of the size of such traditional transducers, conventional ultrasonic probes are disadvantageously required to space the transducers in fairly wide angular increments, thereby leading to non-destructive inspection results that have a relatively low resolution. By way of example, in order to inspect a shear tie that spans 90° and has an arc length of 0.59 inches with an inspection probe that includes five traditional transducers that are each about 0.25 inches in diameter, the transducers which would have to be divided into two or more rows since the cumulative size of the five transducers is more than twice the arc length of the shear tie. Even in this instance in which the inspection probe would include five transducers placed in two or more rows, the transducers would still be placed at angular increments of 18° so as to extend relatively evenly about the shear tie. As such, the resolution of any one transducer of the inspection probe of this example would also be 18°, which may not be sufficient for some applications. In order to improve the resolution of the inspection probe, the inspection probe can include additional transducers which, in turn, creates additional rows of transducers and, in turn, a larger inspection probe, thereby disadvantageously making the inspection probe more difficult to maneuver.

A conventional inspection probe utilized to non-destructively inspect a structure having a curved surface also generally transfers less energy than desired into the structure as a result of the use of traditional transducers that are individually fired or actuated. In an effort to increase the energy transferred into the structure and, thereby, increase the depth and quality of the inspection, the transducers can be actuated with larger driving voltages, and the receiver that receives the signals returning from the structure may be configured to have a higher gain. However, the use of higher driving voltages and higher gains disadvantageously require the inspection probe to consume more energy.

Additionally, ultrasonic inspection probes generally require a couplant, such as water, between the transducers and the structure to be inspected in order to efficiently couple the ultrasonic signals between the transducers and the structure. Typically, water is provided between the inspection probe and the structure such that a pool of water is on the face of each transducer. Since the efficient transmission and reception of the ultrasonic signals are dependant upon the presence of water on the face of each transducer, the inspection speed, that is, the speed at which the inspection probe is capable of being moved along the structure while continuing to effectively interrogate the structure, is limited by the ability to maintain the water in ample supply on the face of the transducers. As the number of transducers increase, such as to five or more, and the speed at which the inspection probe is moved increased, the amount of water required to effectively couple ultrasonic signals into and out of the structure disadvantageously increases. Particularly for hand-held or portable inspection probes, the necessity to provide a sufficient quantity of water may prove quite cumbersome and difficult to manage.

Accordingly, it would be desirable to develop an improved method and apparatus for inspecting workpieces having a curved surface including, for example, a workpiece having a curved surface with portions having different respective radii. In this regard, it would be desirable to provide an improved method and apparatus for inspecting a structure having a curved surface that could provide inspection results with improved resolution, while avoiding excessive energy consumption and couplant usage.

BRIEF SUMMARY OF THE INVENTION

Embodiments of the present invention address at least some of the needs and achieve other advantages by providing an improved non-destructive inspection method, apparatus and system for inspecting a workpiece having a curved surface with at least one predefined radius of curvature. In one embodiment, an apparatus, such as an inspection probe, is provided that includes a housing, a plurality of transducer elements, typically configured in a phased array, carried by the housing and positioned in an arcuate configuration having a predefined radius of curvature and a curved delay line that is also carried by the housing. The curved delay line has an outer arcuate surface having a predefined radius of curvature that matches the predefined radius of curvature of the plurality of elements. The curved delay line also has an inner arcuate surface exposed to the workpiece via a corresponding opening defined by the housing. The inner arcuate surface of the curved delay line has at least one predefined radius of curvature that matches the at least one predefined radius of curvature of the curved surface of the workpiece. In one embodiment, the curved surface of the workpiece includes first and second portions having first and second predefined radii of curvature, respectively, with the first predefined radius of curvature being different than the second predefined radius of curvature. In this embodiment, the inner surface of the curved delay line also includes first and second portions having first and second predefined radii of curvature that match the first and second predefined radii of curvature, respectively, of the curved surface.

The curved delay line may be formed of a flexible material, such as an Aqualine® flexible membrane. As noted above, the curved delay line can be appropriately shaped to match both the curvature of the plurality of elements and the curved surface of the workpiece. In this regard, the respective radii of curvature defined by the inner and outer arcuate surfaces of the curved delay line may be non-concentric.

In accordance with one embodiment, the apparatus, such as the inspection probe, may also include at least one mechanical guide extending outward from the housing and also having a predefined radius of curvature. Further, the apparatus may include a plurality of bearings carried by the housing and configured to be exposed and to ride upon the workpiece. Additionally, the apparatus may include an encoder for providing signals indicative of movement of the housing relative to the workpiece.

In one embodiment, a system for inspecting a workpiece having a curved surface is provided that includes an inspection probe having a plurality of transducer elements, typically configured in a phased array, positioned in an arcuate configuration and a curved delay line as generally described above. The system of this embodiment also includes an excitative source configured to trigger respective ones of the transducers such that the respective transducers emit signals into the workpiece. Additionally, the system of this embodiment can include a computing device configured to receive return signals from the transducers following propagation through the workpiece.

The excitative source may be configured to concurrently trigger a plurality of the transducers. The excitative source may also be configured to sequentially trigger different pluralities of the transducer elements. In this regard, at least some of the elements may be included in at least two of the different pluralities of the elements.

The computing device of the system of this embodiment may be configured to display a representation of the return signals from the elements. In embodiments in which the inspection probe also includes an encoder for providing signals indicative of the movement of the inspection probe relative to the workpiece, the computing device may be in communication with the encoder and may be further configured to associate a location with the return signals based upon the signals provided by the encoder. The computing device may be further configured to issue commands to the excitative source that at least partially control the triggering of the respective elements by the excitative source.

In another embodiment, a method for inspecting a workpiece having a curved surface is provided. In this method, an inspection probe of the type generally described above is positioned upon the curved surface of the workpiece. Thereafter, respective ones of the elements are triggered to emit signals into the workpiece and return signals from the elements following propagation through the workpiece are received. In one embodiment, a plurality of elements are concurrently triggered. In a further embodiment, different pluralities of the elements are sequentially triggered in order to interrogate at least somewhat different portions of the workpiece. In some embodiments, at least some of the elements are included in at least two of the different pluralities of the elements. Following receipt of the return signals, a representation of the return signals may be displayed. Signals indicative of the movement of the inspection probe relative to the workpiece may also be provided, and a location may be correspondingly associated with the return signals based upon the signals indicative of the movement of the inspection probe.

By shaping the curved delay line in such a manner as to match the arcuate configuration of the plurality of elements on one side and to match the curved surface of the workpiece on the other side provides for the efficient transmission of ultrasonic signals into the workpiece and the propagation of return signals from the workpiece, thereby improving the quality of the inspection results and reducing the quantity of couplant that is otherwise required between the inspection probe and the workpiece. Additionally, by positioning the plurality of elements in an arcuate configuration that is spaced from the curved surface of the workpiece by the curved delay line, the inspection apparatus can include additional elements to improve the resolution of the inspection results. Further, by controllably triggering different pluralities of the elements in one embodiment, ample energy may be coupled to the workpiece in order to generate reliable inspection results without requiring increased power consumption as in some conventional inspection devices.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
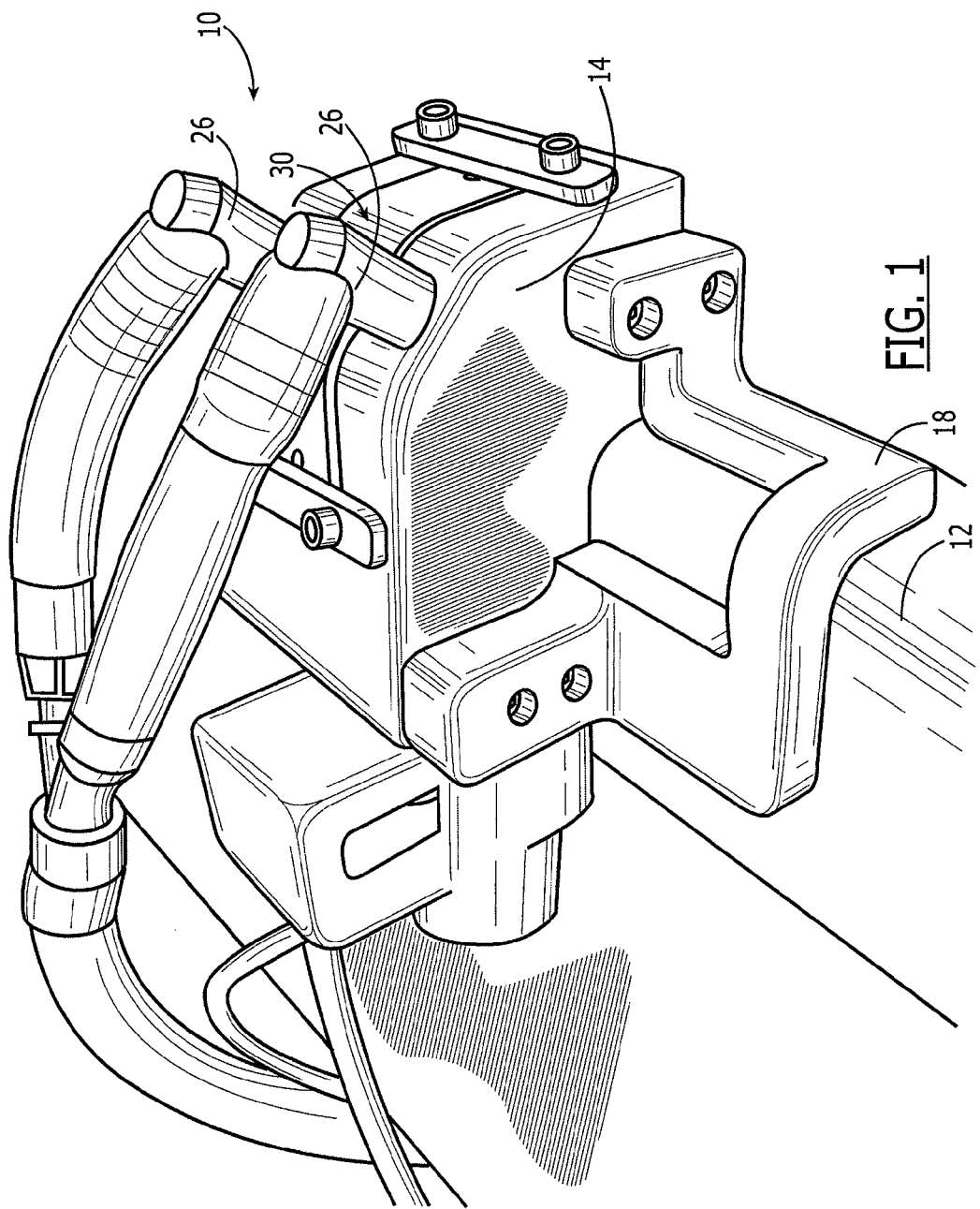
FIG. 1 is a perspective view of an apparatus for inspecting a workpiece having a curved surface in accordance with one embodiment of the present invention.

An apparatus 10, such as an inspection probe, for inspecting a workpiece 12 having a curved surface with at least one predefined radius of curvature is depicted in FIG. 1 in accordance with one embodiment of the present invention. While the workpiece depicted in FIG. 1 is a shear tie, such as employed in the manufacture of aircraft, the apparatus can be employed to inspect a wide variety of other types of workpieces having curved surfaces, including workpieces formed of various materials including composite materials and workpieces designed for various applications, including aircraft, marine vehicles, automobiles, spacecraft and the like, as well as buildings. Still further, the apparatus can inspect a workpiece prior to assembly, following assembly or in both settings, as desired.

While the curved surface of the workpiece 12 may have a single predefined radius of curvature, the curved surface of the workpiece may include two or more portions that each have a different predefined radius of curvature such that the curved surface will be considered to have a composite radii. By way of example, the curved surface may include first and second portions having first and second predefined radii of curvature, respectively, with the first predefined radius of curvature being different than the second predefined radius of curvature.

Figure 2:
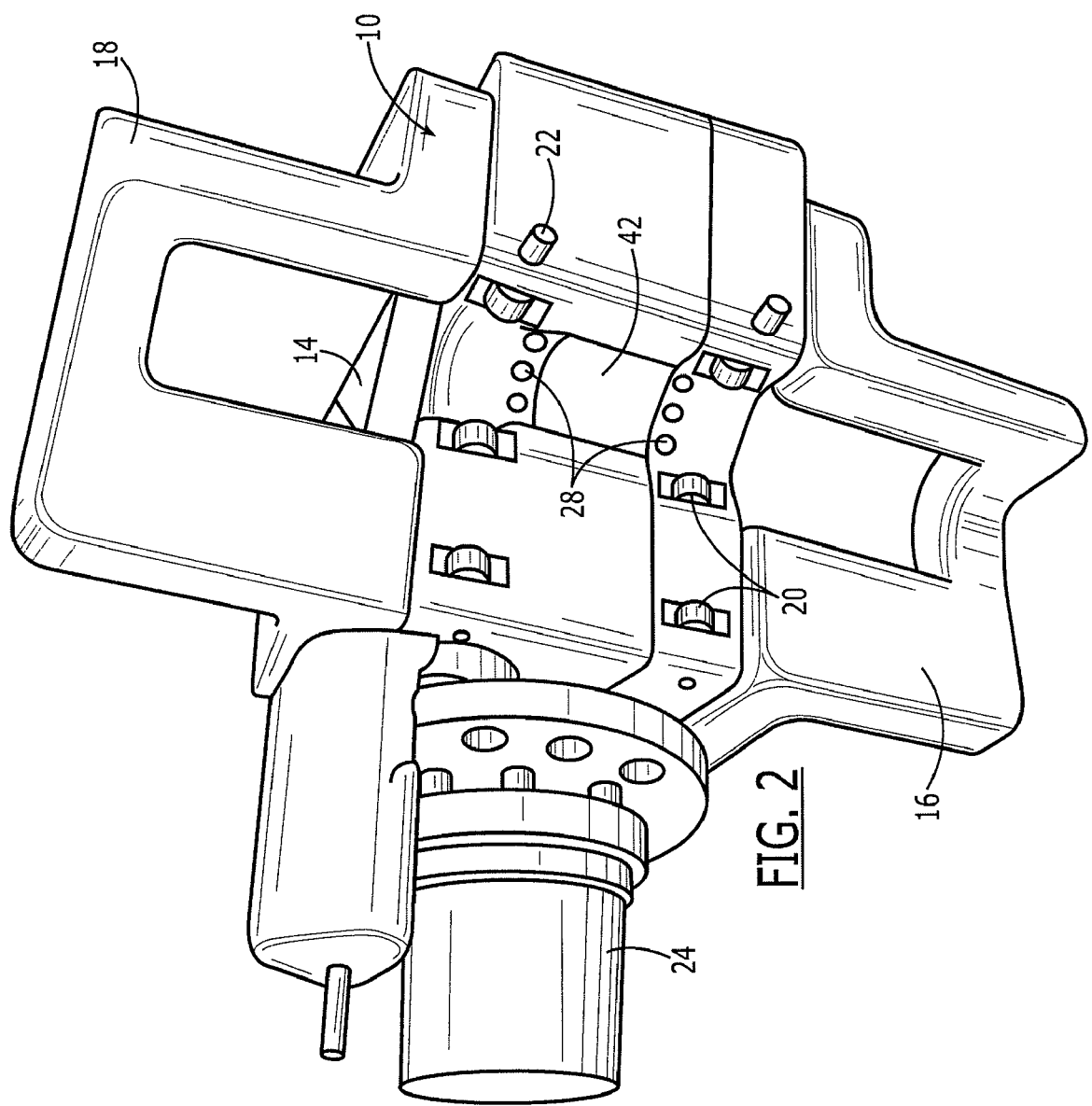
FIG. 2 is a perspective view of the apparatus of FIG. 1 which depicts the portion of the apparatus which faces the curved surface of the workpiece.

As shown in FIGS. 1 and 2, the apparatus 10 includes a housing 14. The housing may have various shapes and sizes. In one embodiment, however, the surface 16 of the housing that faces the workpiece 12 has a shape that generally matches the shape of the workpiece such that the housing can move relatively smoothly over the workpiece and be supported thereon. In order to stabilize and guide the apparatus during the inspection of the workpiece, the apparatus may also include at least one mechanical guide 18 extending outward from the housing. As shown in the embodiment depicted in FIGS. 1 and 2, the apparatus includes a pair of mechanical guides extending outwardly from opposite sides of the housing. Each mechanical guide also generally has a predefined radius of curvature that generally matches the curvature of the workpiece. Although the mechanical guide(s) may extend outwardly from the housing in various directions, the mechanical guides generally extend laterally outward from the housing in a direction that is parallel to the direction in which the apparatus will be moved during the inspection of the workpiece, such as along the length of the shear tie in the exemplary embodiment depicted in FIGS. 1 and 2. In order to decrease the weight and the material requirements of the apparatus, the mechanical guides can define openings therethrough while still providing the desired stabilization and guiding functionality.

As shown in FIG. 2, the apparatus 10 can include a plurality of bearings 20 carried by the housing 14. The bearings are retained by the housing, but are exposed through the surface 16 of the housing that faces the workpiece 12 such that the bearings, as opposed to the housing itself, contact and ride upon the workpiece. Depending upon the anticipated motion of the apparatus relative to the workpiece, the apparatus can include various types of bearings, such as cylindrical bearings mounted upon corresponding axles 22 that are engaged and retained by the housing. Alternatively, ball bearings or other types of bearings can be employed. In addition to or instead of the bearings, the apparatus may include other types of contact members to support the apparatus upon the workpiece including a shoe, a skid, a tread or the like.

The apparatus 10 may also include an encoder 24 for providing signals indicative of the movement of the housing 14 relative to the workpiece 12. As shown in FIG. 2, the encoder may be a wheel encoder. Alternately, the apparatus can include other types of encoders including, for example, a positional encoder, an optical encoder, a linear encoder, a camera, a directional sensor or the like. Regardless of the type of encoder, signals are provided by the encoder from which the movement of the housing from a starting position, i.e., the position of the apparatus at the beginning of the inspection process, can be determined. The signals provided by the encoder do not merely indicate that the housing is moving relative to the workpiece but, instead, provide information relating to the amount or distance by which the housing has moved relative to the workpiece. In instances in which the starting position is pre-established or otherwise known, the signals provided by the encoder that are indicative of the movement of the housing are sufficient to permit the location of the housing and, therefore, the location at which the workpiece is currently being interrogated, to be determined. Alternately, if the starting position is unknown, the signals provided by the encoder permit the relative location of the housing, i.e., relative to the starting position, to be determined.

As shown in FIGS. 1 and 2, the apparatus 10 also generally includes an inlet 26 for the introduction of a couplant, such as water, in one or more outlets 28 and one or more channels or paths defined by the housing between the inlet to the outlet through which the couplant can flow. As shown in FIG. 2, the housing 14 of one embodiment defines a plurality of outlets, each of which receives couplant that is introduced through the inlet and is divided and distributed to each of the outlets by corresponding channels or paths defined by the housing. As such, couplant may be provided via the inlet for distribution via the outlets to the interface between the apparatus and the workpiece 12 under inspection, thereby facilitating efficient transmission and reception of ultrasonic signals to and from the workpiece.

The apparatus 10 also includes a plurality of transducers, such as a plurality of elements 30 of a phased array of transducers, carried by the housing 14 and positioned in an arcuate configuration having a predefined radius of curvature. While the apparatus can include a variety of different types of transducer elements, the apparatus of one embodiment includes elements that function as ultrasonic transducers configured to emit ultrasonic signals into the workpiece 12 and to receive return signals from the workpiece. In one embodiment the phased array is a linear array, such as the linear array bearing Part Number 115000391 provided by General Electric Company, may be utilized. Other suitable linear arrays are provided by Olympus NDT. In this regard, the linear array can include a piece of quartz that is sliced into elements and that is radial in shape. The elements of the phased array may have various pitches, such as 1.5 mm in one embodiment.

Typically, the plurality of elements 30 are positioned in equal angular increments. In one example in which the apparatus 10 includes an array of 64 transducers designed to span an 80° arc, each element is spaced apart by 1.4°. The physical spacing of the elements will vary depending upon the length of the array, but, in one embodiment, the elements are equally spaced at intervals of 0.002 inches. Because the elements are positioned relatively close to one another, both in terms of their angular spacing and their physical spacing, the resulting resolution of the inspection results are improved with the exemplary array of elements described above providing inspection results having a resolution of 1.4°, thereby providing the requisite input for a relatively high definition scan inspection image. Additionally, since the plurality of elements are arranged in arcuate configuration, each element is positioned to emit signals that propagate in a direction approximately normal to that portion of the curved surface of the workpiece that receives the signals emitted by the respective element, thereby further improving the efficiency and quality of the inspection results.

In order to accommodate a relatively large number of elements 30, the plurality of elements must generally be positioned in a spaced relationship from the workpiece 12 and configured to have a focal length that extends into the workpiece. In order to permit the plurality of elements to be sufficiently spaced from the workpiece while avoiding any requirement for an excessive amount of couplant to fill the region between the elements and the workpiece, the apparatus 10 also includes a curved delay line 42 carried by the housing 14 and positioned between the plurality of elements and the surface 16 of the housing that faces the workpiece. In this regard, the curved delay line is exposed to the workpiece through an opening defined by the housing.

The curved delay line 42 is advantageously formed of a material that has approximately the same velocity of propagation for ultrasonic signals as does water. As such, the curved delay line serves to efficiently couple ultrasonic signals to and from the workpiece 12 while reducing the quantity of couplant that is required. In order to further facilitate signal propagation between the inspection probe and the workpiece, couplant, such as water, is provided between the curved delay line and the workpiece. In this regard, it is noted that the outlets 28 are proximate the curved delay line and, in the illustrated embodiment, are positioned on opposite sides of the curved delay line to facilitate the provision of couplant between the curved delay line and the structure. As described below, the curved delay line is also advantageously formed of a flexible material in order to facilitate its manufacture. As such, the curved delay line of one embodiment may be formed of an Aqualine® flexible membrane.

Figure 3:
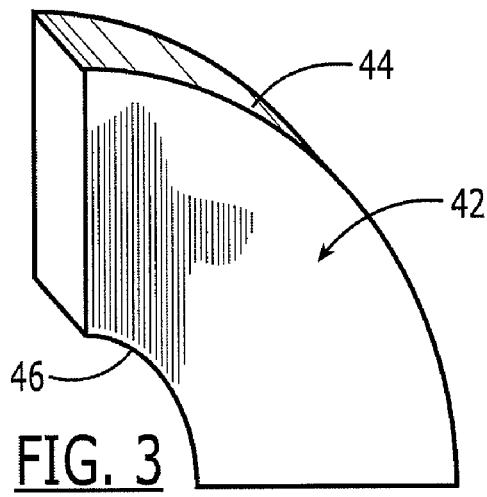
FIG. 3 is a perspective view of a curved delay line of an apparatus for inspecting a workpiece having a curved surface in accordance with one embodiment of the present invention.
Figure 4:
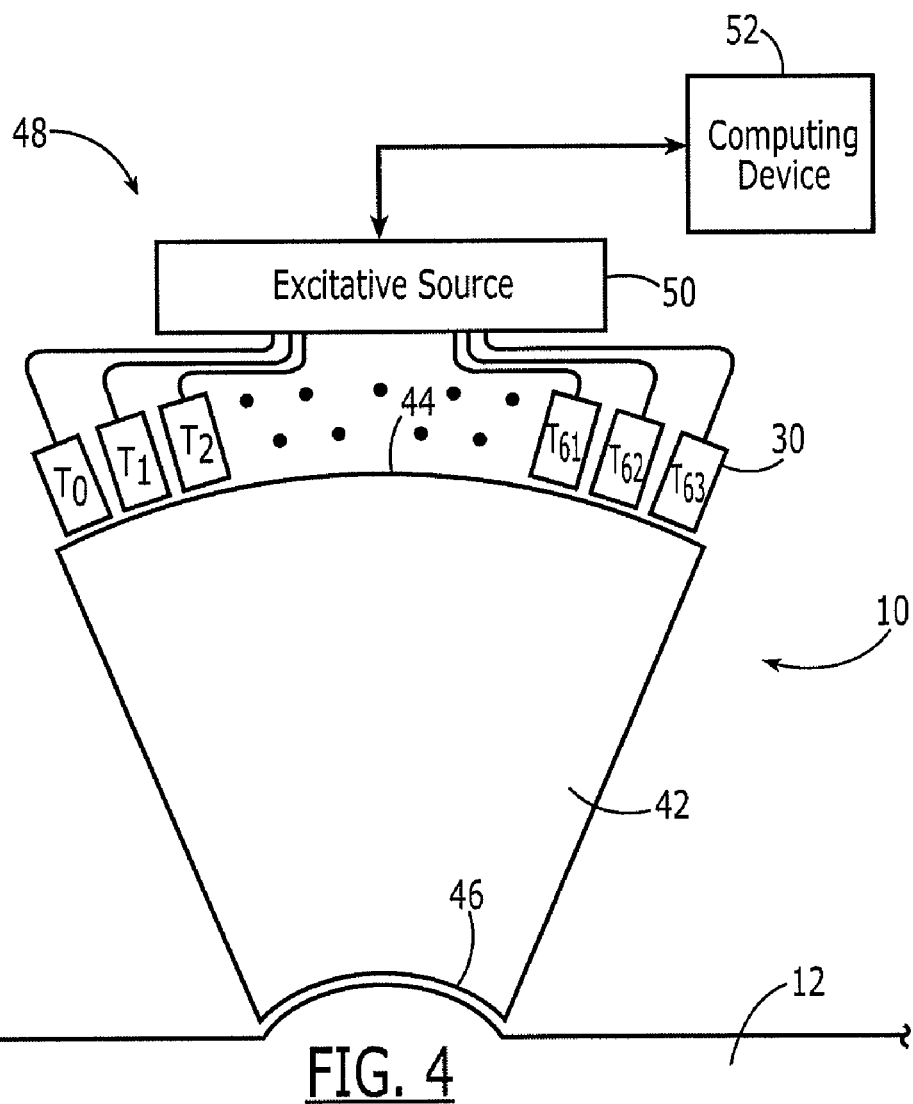
FIG. 4 is a diagrammatic view of a system for inspecting a workpiece having a curved surface in accordance with one embodiment of the present invention.

As shown in FIGS. 3 and 4, a curved delay line 42 has an outer arcuate surface 44 having a predefined radius of curvature that matches the predefined radius of curvature of the plurality of elements 30. The curved delay line also includes an inner arcuate surface 46 that has at least one predefined radius of curvature that matches the at least one predefined radius of curvature of the curved surface of the workpiece. In at least some embodiments, the predefined radius of curvature of the plurality of elements is different than the predefined radius of curvature of the curved surface of the workpiece such that the respective radii of curvature defined by the inner and outer arcuate surfaces of the curved delay line are different and non-concentric.

In instances in which the curved surface of the workpiece 12 include a plurality of portions having different predefined radii of curvature, the inner arcuate surface 46 of the curved delay line 42 may also include a plurality of portions that each have different predefined radii of curvature that match the predefined radius of curvature of the corresponding portions of the curved surface. By way of example in which the curved surface of the workpiece includes first and second portions having first and second predefined radii of curvature, the inner surface of the curved delay line may include first and second portions having first and second predefined radii of curvature that match the first and second predefined radii of curvature, respectively, of the curved surface. Thus, the inner arcuate surface 46 of the curved delay line may also have a composite radii that matches the composite radii of the curved surface of the workpiece.

Since the curved delay line 42 is advantageously formed of a flexible material, the curved delay line of one embodiment is fabricated by cutting a blank to the desired shape of the curved delay line with a water jet cutter. In this manner, the water jet cutter can also define the inner and outer arcuate curved surfaces 44, 46 to have the respective radii of curvature, even if the respective radii of curvature of the inner and outer arcuate surfaces are different.

Figure 5:
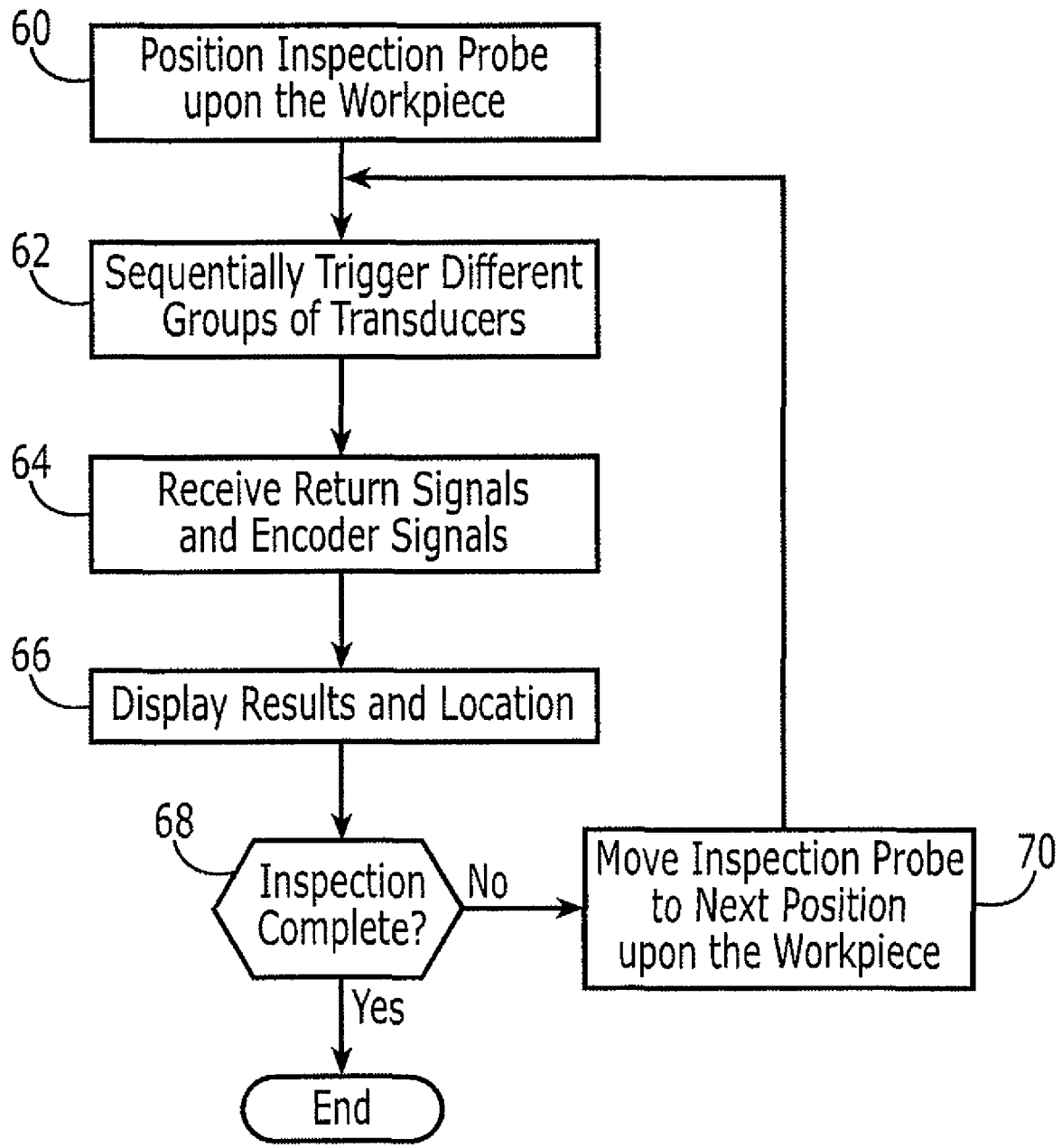
FIG. 5 is a flow chart depicting operations performed to inspect a workpiece having a curved surface in accordance with one embodiment of the present invention.

In operation, the apparatus 10 is positioned upon the curved surface of the workpiece 12 such that the inner arcuate surface 46 of the curved delay line 42 faces the workpiece. See block 60 of FIG. 5. One or more of the elements 30 are then actuated, and ultrasonic signals are transmitted through the curved delay line and into the workpiece and return signals returning from the workpiece propagate through the curved delay line for receipt by the respective element(s). Typically, some couplant, such as a relatively small amount of water, is still provided between the inner arcuate surface of the curved delay line and the workpiece in order to further increase the efficiency with which ultrasonic signals propagate therebetween. By utilizing a curved delay line, however, the flow of couplant is reduced, such to less than twelve fluid ounces per minute in one embodiment.

The transducers 30 may be actuated in various manners. In one embodiment, a system 48 is provided as shown in FIG. 4 that includes an inspection probe 10 of the general type described above. The system of this embodiment also includes an excitative source 50 configured to trigger respective ones of the transducer elements such that the respective elements emit signals into the workpiece. The excitative source may take many forms, including a pulser or an Omniscan instrument manufactured by Olympus NDT. In order to increase the ultrasonic energy with which the workpiece is inspected, the excitative source may be configured to concurrently trigger a plurality of the elements. For example, in the embodiment in which the inspection probe includes an array of 64 elements, the excitative source may be configured to concurrently trigger 8 of the elements at one time. Additionally, the excitative source may be configured to sequentially trigger different pluralities of the elements as shown in block 62 of FIG. 5. In the foregoing exemplary embodiment in which the excitative source concurrently triggered 8 of the 64 elements at one time, the excitative source may be configured to sequentially trigger different groups of 8 elements in order to effectively inspect different portions of the workpiece. Moreover, at least some of the elements may be included in at least two of the different pluralities of the elements. Continuing with the foregoing example in which 64 elements designated $T_0, T_1, T_2, \ldots T_{62}, T_{63}$ are triggered in groups of 8, the excitative source may be configured to initially trigger the elements designated $T_0, T_1, \ldots T_6, T_7$ at a first time, then trigger the elements designed $T_1, T_2, \ldots T_7, T_8$ at a second time, then trigger the elements designed $T_2, T_3, \ldots T_8, T_9$ at a third time and so on until finally triggering a group of elements designed $T_{56}, T_{57}, \ldots T_{62}, T_{63}$ during a 57th time. By concurrently triggering a plurality of transducer elements, the ultrasonic energy within the workpiece is increased, thereby facilitating the inspection of the workpiece without requiring excessive energy to drive or trigger the elements. Additionally, by sequentially triggering different groups of elements that overlap with one another, typically to a large degree, the resolution of the interrogation results is improved.

As shown in FIG. 4, the system 48 may also include a computing device 52, such as a personal computer, a server, a computer workstation, a processor or the like, configured to receive return signals from the transducers following propagation through the workpiece 12. See also block 64 of FIG. 5. In one embodiment, the computing device issues commands to the excitative source 50, such as an Omniscan instrument, instructing the Omniscan instrument to trigger the respective transducer elements, such as in the overlapping sequential pattern described above. Following propagation of the ultrasonic signals through the workpiece, the transducer elements receive the return signals, and the return signals are transmitted to the computing device. The computing device can then store the return signals, such as for future analysis, and/or can display a representation of the return signals for substantially real-time analysis by a technician. The computing device can display the inspection results in various manners, including as a raster strip scan of the return signals following interrogation by each different group of transducers. The computing device can also receive the signals from the encoder 24 indicative of movement of the housing 14 relative to the workpiece. As such, the computing device can associate a location upon the workpiece with the return signals, thereby mapping the return signals onto the workpiece. This location is typically either a location relative to the starting position of the housing upon inception of the inspection process or an exact location in instances in which the starting position is predefined or otherwise known.

As such, the apparatus 10, system 48 and method of the various embodiments of the present invention can inspect a workpiece 12 having a curved surface with relatively high resolution due to the small spacing between the elements 30. By employing a curved delay line 42, however, the elements can be spaced somewhat away from the workpiece while still not requiring an excessive amount of couplant to facilitate propagation of the ultrasonic signals between the inspection probe and the workpiece. Moreover, the elements may be driven or triggered in such a manner as to supply ample ultrasonic energy to the workpiece so as to facilitate reliable inspection results without requiring an excessive amount of excitative energy to trigger the elements.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for inspecting a workpiece having a curved surface with at least one predefined radius of curvature, the apparatus comprising:
    a housing;
    a plurality of transducer elements carried by the housing and positioned in an arcuate configuration having a predefined radius of curvature;
    an excitative source configured to concurrently trigger a respective plurality of the transducer elements such that the respective transducer elements emit signals into the workpiece, wherein the excitative source is configured to sequentially trigger different pluralities of the transducer elements, and wherein at least some of the transducers are included in at least two of the different pluralities of the transducer elements; and
    a curved delay line carried by the housing, the curved delay line having an outer arcuate surface having a predefined radius of curvature that matches the predefined radius of curvature of the plurality of transducer elements, the curved delay line also having an inner arcuate surface exposed to the workpiece via a corresponding opening defined by the housing, the inner arcuate surface of the curved delay line having at least one predefined radius of curvature that matches the at least one predefined radius of curvature of the curved surface of the workpiece,
    wherein an arc defined by the outer arcuate surface across which the transducer elements are positioned is longer than an arc defined by the inner arcuate surface.

2. An apparatus according to claim 1 wherein the respective radii of curvature defined by the inner and outer arcuate surfaces of the curved delay line are non-concentric.

3. An apparatus according to claim 1 wherein the curved delay line is comprised of a flexible material.

4. An apparatus according to claim 1 wherein the curved surface comprises first and second portions having first and second predefined radii of curvature, respectively, wherein the first predefined radius of curvature is different than the second predefined radius of curvature, and wherein the inner surface of the curved delay line also comprises first and second portions having first and second predefined radii of curvature that match the first and second predefined radii of curvature, respectively, of the curved surface.

5. An apparatus according to claim 1 further comprising at least one mechanical guide extending outward from the housing and also having a predefined radius of curvature.

6. An apparatus according to claim 1 further comprising a plurality of bearings carried by the housing and configured to be exposed to and to ride upon the workpiece.

7. An apparatus according to claim 1 further comprising an encoder for providing signals indicative of movement of the housing relative to the workpiece.

8. An apparatus according to claim 1 wherein the curved delay line is tapered outwardly from the inner arcuate surface to the outer arcuate surface, and wherein the plurality of transducer elements are positioned upon the outer arcuate surface so as to span thereacross.

9. An apparatus according to claim 1 wherein the outer and inner arcuate surfaces have respective radii of curvature, and wherein the radius of curvature of the outer arcuate surface is greater than the radius of curvature of the inner arcuate surface.

10. An apparatus according to claim 1 wherein the inner arcuate surface is subtended by the arc defined by the outer arcuate surface.

11. An apparatus according to claim 1 wherein the curved delay line has a velocity of propagation that is approximately equal to that of water.

12. A system for inspecting a workpiece having a curved surface with at least one predefined radius of curvature, the system comprising:
    an inspection probe comprising:
        a plurality of transducer elements positioned in an arcuate configuration having a predefined radius of curvature; and
        a curved delay line having an outer arcuate surface having a predefined radius of curvature that matches the predefined radius of curvature of the plurality of transducer elements, the curved delay line also having an inner arcuate surface having at least one predefined radius of curvature that matches the at least one predefined radius of curvature of the curved surface of the workpiece, wherein an arc defined by the outer arcuate surface across which the transducer elements are positioned is longer than an arc defined by the inner arcuate surface;

an excitative source configured to concurrently trigger a respective plurality of the transducer elements such that the respective transducer elements emit signals into the workpiece, wherein the excitative source is configured to sequentially trigger different pluralities of the transducer elements, and wherein at least some of the transducers are included in at least two of the different pluralities of the transducer elements; and a computing device configured to receive return signals from the transducer elements following propagation through the workpiece.

13. A system according to claim 12 wherein the respective radii of curvature defined by the inner and outer arcuate surfaces of the curved delay line are non-concentric.

14. A system according to claim 12 wherein the curved delay line is comprised of a flexible material.

15. A system according to claim 12 wherein the curved surface comprises first and second portions having first and second predefined radii of curvature, respectively, wherein the first predefined radius of curvature is different than the second predefined radius of curvature, and wherein the inner surface of the curved delay line also comprises first and second portions having first and second predefined radii of curvature that match the first and second predefined radii of curvature, respectively, of the curved surface.

16. A system according to claim 12 wherein the computing device is configured to display a representation of the return signals from the transducer elements.

17. A system according to claim 12 wherein the inspection probe further comprises an encoder for providing signals indicative of movement of the inspection probe relative to the workpiece, and wherein the computing device is in communication with the encoder and is further configured to associate a location with the return signals based upon the signals provided by the encoder.

18. A system according to claim 12 wherein the computing device is further configured to issue commands to the excitative source at least partially controlling triggering of the respective transducer elements by the excitative source.

19. A system according to claim 12 wherein the curved delay line is tapered outwardly from the inner arcuate surface to the outer arcuate surface, and wherein the plurality of transducer elements are positioned upon the outer arcuate surface so as to span thereacross.

20. A system according to claim 12 wherein the outer and inner arcuate surfaces have respective radii of curvature, and wherein the radius of curvature of the outer arcuate surface is greater than the radius of curvature of the inner arcuate surface.

21. A system according to claim 12 wherein the inner arcuate surface is subtended by the arc defined by the outer arcuate surface.

22. A system according to claim 12 wherein the curved delay line has a velocity of propagation that is approximately equal to that of water.

23. A method for inspecting a workpiece having a curved surface with at least one predefined radius of curvature, the method comprising:

positioning an inspection probe upon the curved surface of the workpiece, wherein the inspection probe comprises a plurality of transducer elements positioned in an arcuate configuration having a predefined radius of curvature and a curved delay line having an outer arcuate surface having a predefined radius of curvature that matches the predefined radius of curvature of the plurality of transducer elements and an inner arcuate surface having at least one predefined radius of curvature that matches the at least one predefined radius of curvature of the curved surface of the workpiece, and wherein an arc defined by the outer arcuate surface across which the transducer elements are positioned is longer than an arc defined by the inner arcuate surface;

concurrently triggering a respective plurality of the transducer elements to emit signals into the workpiece, wherein triggering a respective plurality of the transducer elements comprises sequentially triggering different pluralities of the transducer elements, and wherein at least some of the transducers are included in at least two of the different pluralities of the transducer elements; and receiving return signals from the transducer elements following propagation through the workpiece.

24. A method according to claim 23 further comprising displaying a representation of the return signals received from the transducer elements.

25. A method according to claim 23 further comprising:
providing signals indicative of movement of the inspection probe relative to the workpiece; and
associating a location with the return signals based upon the signals indicative of the movement of the inspection probe.

26. A method according to claim 23 wherein the curved delay line is tapered outwardly from the inner arcuate surface to the outer arcuate surface, and wherein the plurality of transducer elements are positioned upon the outer arcuate surface so as to span thereacross.

27. A method according to claim 23 wherein the outer and inner arcuate surfaces have respective radii of curvature, and wherein the radius of curvature of the outer arcuate surface is greater than the radius of curvature of the inner arcuate surface.

28. A method according to claim 23 wherein the inner arcuate surface is subtended by the arc defined by the outer arcuate surface.

29. A method according to claim 23 wherein the curved delay line has a velocity of propagation that is approximately equal to that of water.

* * * * *